United States Patent
Gross et al.

(10) Patent No.: US 8,034,122 B2
(45) Date of Patent: Oct. 11, 2011

(54) BLEACHING AGENT COMPRISING 2-ACYLPYRIDINIUM DERIVATIVES

(75) Inventors: Wibke Gross, Hueckelhoven (DE); Denise Fuhr, Hamburg (DE); Ralph Nemitz, Juechen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/042,615

(22) Filed: Mar. 8, 2011

(65) Prior Publication Data
US 2011/0162671 A1 Jul. 7, 2011

Related U.S. Application Data

(63) Continuation of application No. PCT/EP2009/061389, filed on Sep. 3, 2009.

(30) Foreign Application Priority Data

Sep. 9, 2008 (DE) .......................... 10 2008 046 433

(51) Int. Cl.
*D06L 3/00* (2006.01)
(52) U.S. Cl. .......................... 8/101; 8/107; 8/109; 8/111
(58) Field of Classification Search .............. 8/101, 107, 8/109, 111
See application file for complete search history.

(56) References Cited

U.S. PATENT DOCUMENTS

| | | | |
|---|---|---|---|
| 6,371,993 B1 * | 4/2002 | Moeller et al. ..................... | 8/407 |
| 2005/0262647 A1 | 12/2005 | Hoeffkes et al. | |

FOREIGN PATENT DOCUMENTS

| | | |
|---|---|---|
| AU | 730455 B2 | 5/2000 |
| DE | 10148845 A1 | 4/2003 |
| DE | 102007047685 A1 | 7/2008 |
| EP | 1882495 A2 | 1/2008 |
| EP | 1905418 A2 | 4/2008 |
| WO | 2010054981 A2 | 5/2010 |

OTHER PUBLICATIONS

STIC Search Report dated May 3, 2011.*
Schrader, Karlheinz. Grundlagen und Rezepturen der Kosmetika (Fundamentals and Formulations of Cosmetics), 2, Hüthig Buch Verlag GmbH, Heidelberg 1989.
Umbach, W. Kosmetik Entwicklung, Herstellung und Anwendung kosmetischer Mittel, Georg Thieme Verlag, 1995.
Römp-Lexikon. Lexicon of Chemistry. George Thieme Verlag, vol. 10, 1997, pp. 1764.

* cited by examiner

*Primary Examiner* — Eisa B Elhilo
(74) *Attorney, Agent, or Firm* — David P. LeCroy

(57) ABSTRACT

Agent for lightening keratin fibers containing in a cosmetic carrier (1) at least one cationic 2-acylpyridinium derivative of formula (I),

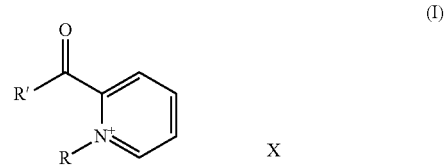

wherein R is a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_1$-$C_6$ alkyl group, an aryl $C_1$-$C_6$ alkyl group, a heteroaryl $C_1$-$C_6$ alkyl group, a mono- or di-($C_1$-$C_6$ alkyl)amino $C_2$-$C_6$ alkyl group, a 3-oxobutyl group, a 2-oxopropyl group, an aryl group or a heteroaryl group, R' is a $C_4$-$C_4$ alkyl group, a $C_2$-$C_6$ hydroxyalkyl group or a $C_1$-$C_6$ alkoxy $C_2$-$C_6$ alkyl group, and $X^-$ is a physiologically acceptable anion, (2) at least one alkyl ether sulfate, and (3) an oxidizing agent, especially hydrogen peroxide.

15 Claims, No Drawings

BLEACHING AGENT COMPRISING 2-ACYLPYRIDINIUM DERIVATIVES

CROSS REFERENCE TO RELATED APPLICATIONS

The present application is a continuation of International Patent Application No. PCT/EP2009/061389 filed 3 Sep. 2009, which claims priority to German Patent Application No. 10 2008 046 433.3 filed 9 Sep. 2008, both of which are incorporated herein by reference.

The present invention relates to agents for lightening keratin fibers (i.e., agents for use on keratin fibers), particularly human hair, containing cationic 2-acylpyridinium derivatives, an anionic surfactant chosen from alkyl ether sulfates, and hydrogen peroxide for lightening hair, as well as the use thereof to lighten keratin fibers and a corresponding method.

Changing the shape and color of hair is an important area of modern cosmetics. It allows the appearance of the hair to be adapted to the latest fashion trends as well as to the personal preferences of the individual. Permanent wave methods and other methods of changing the shape of hair can be used almost regardless of the type of hair being treated. By contrast, coloring and bleaching methods are limited to certain natural hair colors. The basic principles of bleaching methods are known to one skilled in the art and can be researched in relevant monographs by, for example, Kh. Schrader, *Grundlagen and Rezepturen der Kosmetika*, $2^{nd}$ Ed. (1989), Dr. Alfred Hiithig Verlag, Heidelberg, or W. Umbach (Ed.), *Kosmetik*, $2^{nd}$ Ed. (1995), Georg Thieme Verlag, Stuttgart, New York.

In addition to coloring their hair, many consumers also wish to lighten or bleach their natural hair color because blonde hair is considered attractive and desirable from a fashion perspective. A variety of bleaching agents with varying bleaching capacity are commercially available for this purpose. Oxidizing agents present in these products lighten the hair fiber by oxidative breakdown of the hair's natural pigment, melanin. For a moderate bleaching effect, the use of hydrogen peroxide—optionally with the use of ammonia or other alkalizing agents—is sufficient as an oxidizing agent on its own. For a stronger bleaching effect, a mixture of hydrogen peroxide and peroxodisulfate salts and/or peroxomonosulfate salts is conventionally used. Unfortunately, lightening is also associated with hair damage, as the natural coloring components of the hair as well as other structural constituents of the hair are damaged by oxidation. The extent of damage can range from coarse, brittle and tangled hair, through reduced resistance and breaking strength of the hair, to breakage of the hair. The larger the amount of hydrogen peroxide and optionally peroxodisulfates that is used, the greater the damage that is generally caused to the keratin fiber. Hair coloring or lightening agents that demonstrate good lightening capacity without damaging the hair fiber have hitherto been unknown.

Before being used on human hair, lightening agents in solid or paste form are conventionally mixed with dilute aqueous hydrogen peroxide solution. This mixture is then applied to the hair and rinsed out again after a certain contact time. The contact time on the hair required to achieve complete lightening is from about 30 to about 40 minutes. Obviously, there is a need among users of these bleaching agents to reduce this contact time.

Bleaching processes on keratin fibers conventionally take place in an alkaline pH range, particularly from 9.0 to 10.5. An alkaline pH is necessary to ensure that the external cuticle opens, allowing the active species (dye intermediates and/or hydrogen peroxide) to penetrate into the hair. Ammonia is typically used as the alkalizing agent. However, it has the disadvantage for the user of an intense odor and possible irritation through to skin irritation and skin sensitization.

Although bleaching agents hitherto available on the market generally have good lightening capacity, they are not regarded as ideal due to their hair damage, long application times and possible skin irritation caused by the high concentrations of oxidizing and alkalizing agents.

Use of cationic acylpyridinium derivatives in hair coloring is known, for example, from German Patent Application Publication Nos. DE 10148845 A1 or DE 10261656 A1. In both documents, these derivatives are used together with at least a second coloring component as an agent to color and hence increase the color intensity of the hair. It has not been apparent from the prior art that these 2-acylpyridinium derivatives can be used in specific combination with anionic surfactants of the alkyl ether sulfate type and hydrogen peroxide for bleaching hair with very good decolorizing power.

The present invention provides agents for lightening or bleaching hair which, in their lightening capacity, are comparable with or superior to conventional agents on the market yet at the same time give rise to reduced hair damage.

It has now been found that use of a combination of cationic 2-acylpyridinium compounds according to general structure (I) below, at least one anionic surfactant chosen from fatty alcohol ether sulfates, and hydrogen peroxide lightens hair much more strongly than possible through use of a comparable amount of hydrogen peroxide alone.

The amount of oxidizing agent used can be reduced due to the improved bleaching capacity obtained with the use of the agent according to the invention, thus minimizing the hair damage. The contact time necessary to achieve a lightening effect corresponding to the prior art can also be shortened in this way.

Agents according to the invention decolorize the natural dye melanin by oxidation. Without the presence of additional dyes/dye intermediates, the active ingredient combination according to the invention does not visibly form any dye in the keratin-containing fiber. Synthetic dyes previously present on or in the keratin-containing fiber can also be bleached out with the aid of the agents.

The invention thus firstly provides an agent for lightening keratin fibers, wherein it contains in a cosmetic carrier—
i) at least one cationic 2-acylpyridinium derivative of formula (I),

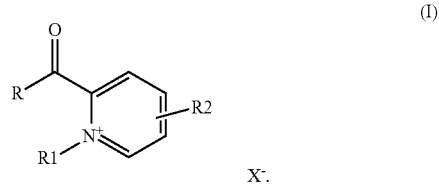

wherein
R is a $C_1$-$C_4$ alkyl group, a $C_2$-$C_6$ hydroxyalkyl group or a $C_1$-$C_6$ alkoxy $C_2$-$C_6$ alkyl group,
R1 is a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_1$-$C_6$ alkyl group, an aryl $C_1$-$C_6$ alkyl group, a heteroaryl $C_1$-$C_6$ alkyl group, a mono- or di-($C_1$-$C_6$ alkyl)amino $C_2$-$C_6$ alkyl group, a 3-oxobutyl group, a 2-oxopropyl group, an aryl group or a heteroaryl group, R2 is hydrogen, a halogen, a nitrile group, a nitro group, an amino group, a mono- or di-($C_1$-$C_6$-alkyl)amino group, a hydroxyl group, a $C_1$-$C_6$ alkoxy group, a $C_1$-$C_6$ alkyl group, a partially or completely halogenated $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a $C_1$-$C_6$ alkoxycarbonyl group, a carboxyl group, a carbamoyl group or an acyl group R'C(O), in which R' denotes a $C_1$-$C_4$ alkyl group, a $C_2$-$C_6$ hydroxyalkyl group or a $C_1$-$C_6$ alkoxy $C_2$-$C_6$ alkyl group, and $X^-$ is a physiologically acceptable anion, (ii) at least one anionic surfactant chosen from alkyl ether sulfates according to the formula

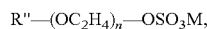

R"—(OC$_2$H$_4$)$_n$—OSO$_3$M, wherein R" is a linear or branched, saturated or optionally unsaturated $C_8$-$C_{30}$ alkyl chain, n is a number greater than 2 and M is hydrogen or a physiologically acceptable cation, and (iii) hydrogen peroxide or a solid addition compound of hydrogen peroxide with inorganic or organic compounds.

The term "keratin fibers" refers to fur, wool, feathers, and particularly human hair. Although the agents are primarily suitable for lightening keratin fibers, there is nothing in general to preclude their use in other fields.

Agents according to the invention contain active ingredients in a cosmetic carrier. This cosmetic carrier is preferably aqueous, alcoholic or aqueous-alcoholic. For the purposes of hair bleaching, such carriers are creams, emulsions, gels or surfactant-containing foaming solutions, such as shampoos, foam aerosols or other preparations suitable for use on hair. For storage purposes, however, it is also possible to provide a formulation in powder or tablet form, which is preferred for lightening agents. Before use, it is mixed in an aqueous solvent or with organic solvents or with mixtures of water and organic solvents to obtain an application mixture. An aqueous carrier contains within the meaning of the invention at least 40 wt. %, particularly at least 50 wt. % of water. According to the present invention, aqueous-alcoholic carriers are hydrous compositions containing 3 to 70 wt. % of a $C_1$ to $C_4$ alcohol, particularly ethanol or isopropanol. The agents can also contain further organic solvents such as 4-methoxybutanol, ethyl diglycol, 1,2-propylene glycol, n-propanol, n-butanol, n-butylene glycol, glycerol, diethylene glycol monoethyl ether, and diethylene glycol mono-n-butyl ether. All water-soluble organic solvents are preferred here. Preferred agents additionally contain a non-aqueous solvent, wherein particularly preferred agents contain the solvent in a concentration of 0.1 to 30 wt. %, preferably in a concentration of 1 to 20 wt. %, most particularly preferably in a concentration of 2 to 10 wt. %, relative in each case to the agent.

Examples of residues cited as substituents of the compounds of formula (I) are listed below:

Examples of $C_1$ to $C_4$ alkyl residues are the —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$ groups.

Examples of $C_1$ to $C_6$ alkyl residues are the —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —(CH$_2$)$_4$CH$_3$, —(CH$_2$)$_5$CH$_3$ groups. Particularly preferred alkyl residues are methyl and ethyl.

Examples of partially or completely halogenated $C_1$-$C_6$ alkyl residues are the —CH$_2$F, —CH$_2$Cl, —CF$_3$, —CH$_2$CF$_3$, —CF$_2$CF$_3$ or —CH(CF$_3$)$_2$ groups, particularly —CF$_3$.

Examples of a $C_2$-$C_6$ alkenyl group are prop-2-enyl (allyl group), 2-methyl prop-2-enyl, a but-3-enyl, but-2-enyl, pent-4-enyl or pent-3-enyl. The prop-2-enyl group is particularly preferred in this context.

Examples of a $C_1$-$C_6$ alkoxy group are —OCH$_3$, —OCH$_2$CH$_3$, —OCH$_2$CH$_2$CH$_3$, —OCH(CH$_3$)$_2$ or —OC(CH$_3$)$_3$, the methoxy group (—OCH$_3$) being preferred.

Examples of a $C_1$-$C_6$ alkoxycarbonyl group are C(O)OCH$_3$, —C(O)OCH$_2$CH$_3$, —C(O)OCH$_2$CH$_2$CH$_3$, —C(O)OCH(CH$_3$)$_2$ or —C(O)OC(CH$_3$)$_3$, the methoxycarbonyl group (—C(O)OCH$_3$) being preferred.

Examples of a halogen are fluorine, chlorine, bromine or iodine, particularly fluorine and chlorine.

—CH$_2$CH$_2$OH, —CH$_2$CH$_2$CH$_2$OH, —CH$_2$CH(OH)CH$_3$, —CH$_2$CH$_2$CH$_2$CH$_2$OH can also be used as preferred examples of a $C_2$-$C_6$ hydroxyalkyl group, —CH$_2$CH$_2$OH being preferred.

Examples of $C_1$-$C_6$ alkoxy $C_2$-$C_6$ alkyl groups are —CH$_2$CH$_2$OCH$_3$, —CH$_2$CH$_2$CH$_2$OCH$_3$, —CH$_2$CH$_2$OCH$_2$CH$_3$, —CH$_2$CH$_2$CH$_2$OCH$_2$CH$_3$, —CH$_2$CH$_2$OCH(CH$_3$)$_2$, —CH$_2$CH$_2$CH$_2$OCH(CH$_3$)$_2$.

Examples of a carboxy $C_1$-$C_6$ alkyl group are carboxymethyl, 2-carboxyethyl or 3-carboxypropyl.

Examples of aryl $C_1$-$C_6$ alkyl groups are benzyl and 2-phenylethyl.

Examples of a heteroaryl $C_1$-$C_6$ alkyl group are the pyridin-2-yl methyl group, the pyridin-3-yl methyl group, the pyridin-4-yl methyl group, the pyrimidin-2-yl methyl group, the pyrrol-1-yl methyl group, the pyrrol-1-yl ethyl group, the pyrazol-1-yl methyl group or the pyrazol-1-yl ethyl group.

Examples of a mono- or di-($C_1$-$C_6$ alkyl)amino $C_2$-$C_6$ alkyl group are the 2-methylaminoethyl group, 2-ethylaminoethyl group, 2-dimethylaminoethyl group, 2-diethylaminoethyl group, 3-methylaminopropyl group, 3-dimethylaminopropyl group, 2-(piperidin-1-yl)ethyl group, 2-(pyrrolidin-1-yl) ethyl group, 2-(morpholin-1-yl)ethyl group and 2-bis-(2-hydroxyethyl)aminoethyl group, the 2-dimethylaminoethyl group and the 2-diethylaminoethyl group being particularly preferred.

An example of an aryl group is the phenyl group, the 1-naphthyl group or the 2-naphthyl group.

Examples of a heteroaryl group are the pyridin-2-yl group, the pyridin-3-yl group, the pyridin-4-yl group, the pyrimidin-2-yl group, the pyrrol-1-yl group, the pyrrol-2-yl group, the pyrazol-1-yl group, the pyrazol-3-yl group or the pyrazol-2-yl group.

Agents according to the invention contain at least three constituents: at least one cationic 2-acylpyridinium derivative of formula (I), at least one anionic surfactant of the fatty alcohol ether sulfates, and hydrogen peroxide. The agents can also be "application mixtures", that is, agents which are packaged separately (for stability reasons, for example) but are mixed together before use to form an application mixture and then applied.

Suitable compounds according to formula (I) are preferably those wherein R1 is a $C_1$-$C_6$ alkyl group, a $C_2$-$C_6$ alkenyl group or a $C_2$-$C_6$ hydroxyalkyl group. It is preferable in particular for R1 to be a $C_1$-$C_6$ alkyl group, particularly preferably methyl.

It is furthermore preferable according to the invention for R2 in formula (I) to be hydrogen, a $C_1$-$C_6$ alkyl group or an acyl group R'C(O), in which R' is a $C_1$-$C_4$ alkyl group. R2 particularly preferably is hydrogen or an acetyl group, which means that R' in the acyl group R'C(O) is methyl.

Preferably, the anion $X^-$ according to formula (I) is chosen from halide, particularly chloride, bromide and iodide, benzenesulfonate; p-toluenesulfonate, alkylsulfonate, trifluoromethanesulfonate, acetate, trifluoroacetate, perchlorate, ½ sulfate, hydrogen sulfate, tetrafluoroborate, hexafluorophosphate or tetrachlorozincate. It is particularly preferable for the physiologically acceptable anion X⁻ to be a halide ion (particularly chloride or bromide), hydrogen sulfate, ½ sulfate, p-toluenesulfonate, benzenesulfonate or acetate.

Particularly preferred cationic 2-acylpyridinium derivatives of general formula (I) are

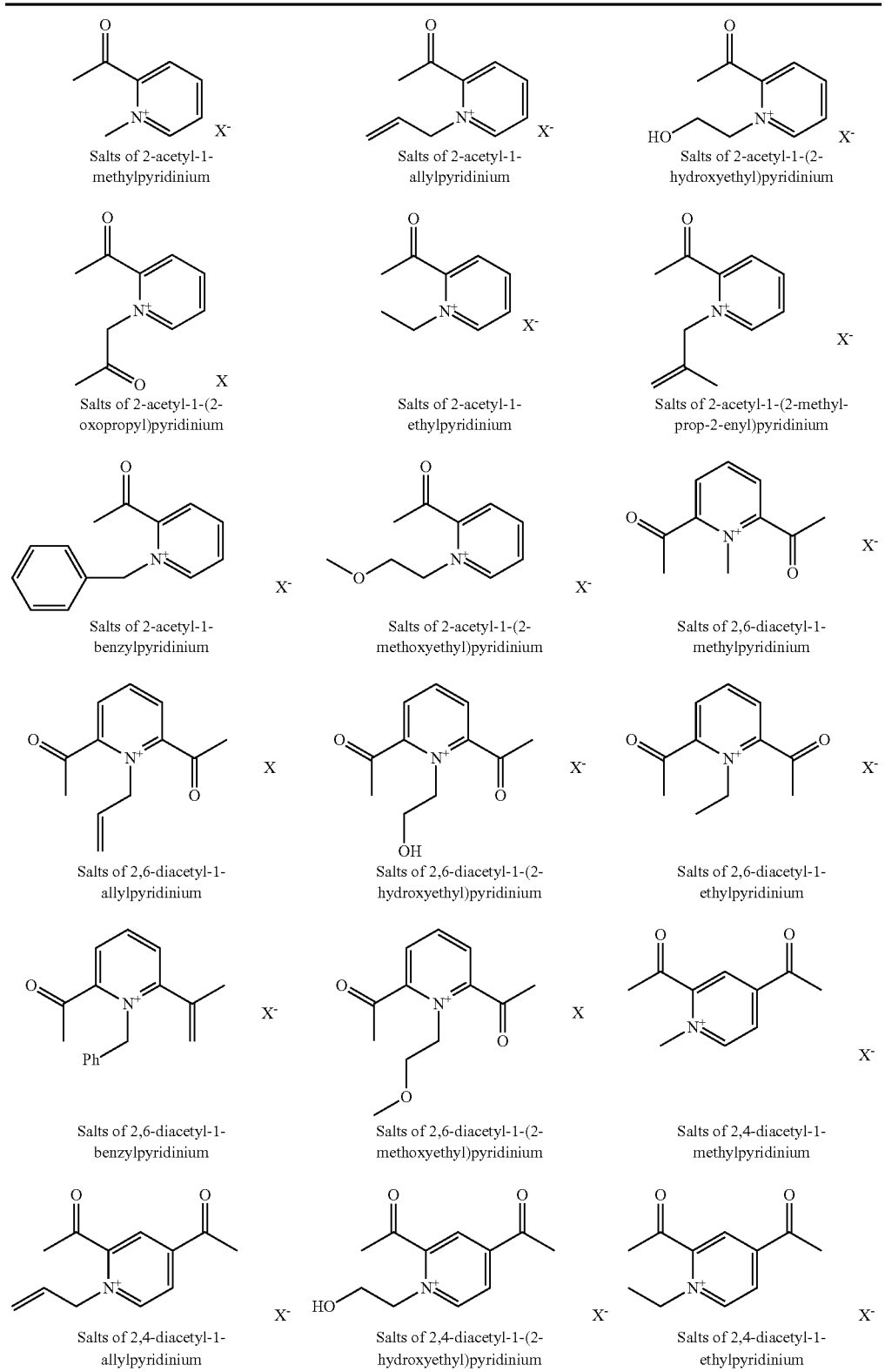

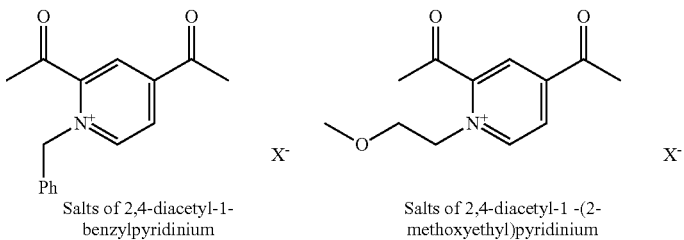

Salts of 2,4-diacetyl-1-benzylpyridinium

Salts of 2,4-diacetyl-1-(2-methoxyethyl)pyridinium wherein $X^-$ in each case assumes the meanings according to structure (I) or the meaning of the aforementioned preferred embodiments.

In summary, preferred agents are those wherein the cationic 2-acylpyridinium derivative of general structure (I) contain at least one compound from 2-acetyl-1-methylpyridinium-p-toluenesulfonate, 2-acetyl-1-methylpyridinium benzenesulfonate, 2-acetyl-1-methylpyridinium bromide, 2-acetyl-1-methylpyridinium chloride, 2-acetyl-1-methylpyridinium hydrogen sulfate, 2-acetyl-1-methylpyridinium acetate, 2-acetyl-1-allylpyridinium-p-toluenesulfonate, 2-acetyl-1-allylpyridinium benzenesulfonate, 2-acetyl-1-allylpyridinium bromide, 2-acetyl-1-allylpyridinium chloride, 2-acetyl-1-allylpyridinium hydrogen sulfate, 2-acetyl-1-allylpyridinium acetate, 2-acetyl-1-(2-hydroxyethyl)pyridinium-p-toluenesulfonate, 2-acetyl-1-(2-hydroxyethyl)pyridinium benzenesulfonate, 2-acetyl-1-(2-hydroxyethyl)pyridinium bromide, 2-acetyl-1-(2-hydroxyethyl)pyridinium chloride, 2-acetyl-1-(2-hydroxyethyl)pyridinium hydrogen sulfate, 2-acetyl-1-(2-hydroxyethyl)pyridinium acetate, 2-acetyl-1-(2-oxopropyl)pyridinium-p-toluenesulfonate, 2-acetyl-1-(2-oxopropyl)pyridinium benzenesulfonate, 2-acetyl-1-(2-oxopropyl)pyridinium bromide, 2-acetyl-1-(2-oxopropyl)pyridinium chloride, 2-acetyl-1-(2-oxopropyl)pyridinium hydrogen sulfate, 2-acetyl-1-(2-oxopropyl)pyridinium acetate, 2-acetyl-1-ethylpyridinium-p-toluenesulfonate, 2-acetyl-1-ethylpyridinium benzenesulfonate, 2-acetyl-1-ethylpyridinium bromide, 2-acetyl-1-ethylpyridinium chloride, 2-acetyl-1-ethylpyridinium hydrogen sulfate, 2-acetyl-1-ethylpyridinium acetate, 2-acetyl-1-(2-methylprop-2-enyl)pyridinium-p-toluenesulfonate, 2-acetyl-1-(2-methylprop-2-enyl)pyridinium benzenesulfonate, 2-acetyl-1-(2-methylprop-2-enyl)pyridinium bromide, 2-acetyl-1-(2-methylprop-2-enyl)pyridinium chloride, 2-acetyl-1-(2-methylprop-2-enyl)pyridinium hydrogen sulfate, 2-acetyl-1-(2-methylprop-2-enyl)pyridinium acetate, 2-acetyl-1-benzylpyridinium-p-toluenesulfonate, 2-acetyl-1-benzylpyridinium benzenesulfonate, 2-acetyl-1-benzylpyridinium bromide, 2-acetyl-1-benzylpyridinium chloride, 2-acetyl-1-benzylpyridinium hydrogen sulfate, 2-acetyl-1-benzylpyridinium acetate, 2-acetyl-1-(2-methoxyethyl)pyridinium-p-toluenesulfonate, 2-acetyl-1-(2-methoxyethyl)pyridinium benzenesulfonate, 2-acetyl-1-(2-methoxyethyl)pyridinium bromide, 2-acetyl-1-(2-methoxyethyl)pyridinium chloride, 2-acetyl-1-(2-methoxyethyl)pyridinium hydrogen sulfate, 2-acetyl-1-(2-methoxyethyl)pyridinium acetate, 2,4-diacetyl-1-methylpyridinium-p-toluenesulfonate, 2,4-diacetyl-1-methylpyridinium benzenesulfonate, 2,4-diacetyl-1-methylpyridinium bromide, 2,4-diacetyl-1-methylpyridinium chloride, 2,4-diacetyl-1-methylpyridinium hydrogen sulfate, 2,4-diacetyl-1-methylpyridinium acetate, 2,6-diacetyl-1-methylpyridinium-p-toluenesulfonate, 2,6-diacetyl-1-methylpyridinium benzenesulfonate, 2,6-diacetyl-1-methylpyridinium bromide, 2,6-diacetyl-1-methylpyridinium chloride, 2,6-diacetyl-1-methylpyridinium hydrogen sulfate, 2,6-diacetyl-1-methylpyridinium acetate, 2,6-diacetyl-1-(2-hydroxyethyl)pyridinium-p-toluenesulfonate, 2,6-diacetyl-1-(2-hydroxyethyl)pyridinium benzenesulfonate, 2,6-diacetyl-1-(2-hydroxyethyl)pyridinium bromide, 2,6-diacetyl-1-(2-hydroxyethyl)pyridinium chloride, 2,6-diacetyl-1-(2-hydroxyethyl)pyridinium hydrogen sulfate and 2,6-diacetyl-1-(2-hydroxyethyl)pyridinium acetate.

Of this group the following acetylpyridinium salts are explicitly most particularly preferred: 2-acetyl-1-methylpyridinium-p-toluenesulfonate, 2-acetyl-1-methylpyridinium benzenesulfonate, 2-acetyl-1-methylpyridinium bromide, 2-acetyl-1-methylpyridinium chloride, 2-acetyl-1-methylpyridinium hydrogen sulfate, 2-acetyl-1-methylpyridinium acetate, 2,6-diacetyl-1-methylpyridinium-p-toluenesulfonate, 2,6-diacetyl-1-methylpyridinium benzenesulfonate, 2,6-diacetyl-1-methylpyridinium bromide, 2,6-diacetyl-1-methylpyridinium chloride, 2,6-diacetyl-1-methylpyridinium hydrogen sulfate and 2,6-diacetyl-1-methylpyridinium acetate.

Unless explicitly stated otherwise, all amounts given below refer to the total weight of the ready-to-use agent.

The agents preferably contain 2-acylpyridinium derivatives of general structure (1) in an amount from 0.01 to 25 wt. %, particularly 0.1 to 10 wt. %, based on total weight of the agent.

As a second constituent of the agent, at least one anionic surfactant is included chosen from alkyl ether sulfates according to the formula $R''-(OCH_2CH_2)_n-OSO_3M$, wherein $R''$ is a linear or branched, saturated or optionally unsaturated $C_8-C_{30}$ alkyl chain, n is a number greater than 2 and M is hydrogen or a physiologically acceptable cation.

Physiologically acceptable cations according to the invention are physiologically acceptable inorganic cations, the charge for polyvalent cations being adjusted according to the stoichiometry. Preferred inorganic cations are ammonium, alkali metal cations, particularly Na or $K^+$, alkaline-earth metal cations, particularly $½Mg^{2+}$ or $½Ca^{2+}$, or $Zn^{2+}$, with $Na^+$ being particularly preferred.

Physiologically acceptable cations according to the invention are furthermore organic cations such as primary, secondary, tertiary or quaternary ammonium ions, particularly mono-, di-, tri- or tetraalkyl ammonium. Suitable organic cations are furthermore hydroxyalkylammonium ions, such as the mono- or tri-(2-hydroxyethyl)ammonium ion (cations of monoethanolamine or triethanolamine).

Alkyl ether sulfates ("ether sulfates") are typically produced in industry by $SO_3$ or chlorosulfonic acid (CSA) sulfatization of fatty alcohol or oxo alcohol polyglycol ethers followed by neutralization. Preferred examples are sulfates in the form of their sodium and/or magnesium salts of ethoxylated addition products of at least 2 ethylene oxide (expressed by the number n) with hexanol, octanol, 2-ethylhexyl alcohol, decanol, lauryl alcohol, isotridecyl alcohol, myristyl alcohol, cetyl alcohol, stearyl alcohol, isostearyl alcohol, eicosyl alcohol or technical mixtures thereof. These are formed, for example, in the high-pressure hydrogenation of technical methyl esters based on fats and oils or aldehydes from the Roelen oxo-synthesis and as a monomer fraction in the dimerization of unsaturated fatty alcohols. Technical fatty alcohols having 12 to 18 carbon atoms, such as coconut, palm, palm kernel or tallow fatty acids, are preferred.

Preferred alkyl ether sulfates of the formula R"—$(OCH_2CH_2)_n$—$OSO_3M$ have the characterizing feature that R" is an optionally branched $C_8$-$C_{22}$ alkyl group, particularly lauryl, myristyl, cetyl, stearyl or a technical mixture containing such alkyl residues, as with coconut, palm, palm kernel or tallow fatty alcohol.

It has been found that alkyl ether sulfates having a high degree of ethoxylation are particularly suitable for achieving an additional intensification of the lightening capacity. Alkyl ether sulfates of the formula R"—$(OCH_2CH_2)_n$—$OSO_3M$ that can advantageously be used are those wherein n is a number from 16 to 50, particularly 20 to 40, and most particularly preferably from 25 to 35. Ether sulfates can have both a conventional and a narrow homolog distribution.

Alkyl ether sulfates of the formula R"—$(OCH_2CH_2)_n$—$OSO_3M$ are most particularly preferred wherein R" is an optionally branched $C_8$-$C_{22}$ alkyl group and n is a number from 16 to 50, particularly 20 to 40, and most particularly preferably from 25 to 35.

Preferred alkyl ether sulfates according to the invention are furthermore those compounds according to the formula R"—$(OCH_2CH_2)_n$—$OSO_3M$ wherein R" is a $C_{10}$-$C_{18}$ alkyl group and n is a number from 25 to 35.

Use of ether sulfates based on adducts of an average of 30 mol of ethylene oxide with technical $C_{12}$-$C_{14}$ or $C_{12}$-$C_{18}$ coconut fatty alcohol fractions is particularly preferred, particularly in the form of their sodium and/or magnesium salts.

A particularly preferred alkyl ether sulfate according to the invention has the INCI name Sodium Coceth-30 sulfate and is sold by Cognis under the trade name Disponil® FES 77 as a 31-33 wt. % aqueous solution.

Alkyl ether sulfates according to the invention are preferably used within certain quantity ranges. Preferred agents contain at least one alkyl ether sulfate in an amount of 0.01 to 15 wt. %, particularly 0.1 to 10 wt. % and particularly preferably 0.5 to 5.0 wt. %, based on total weight of the ready-to-use agent.

Hydrogen peroxide is present in agents according to the invention as a third ingredient. Hydrogen peroxide itself is preferably used as an aqueous solution. Hydrogen peroxide can, however, also be used in the form of a solid addition compound of hydrogen peroxide with inorganic or organic compounds, such as sodium perborate, sodium percarbonate, magnesium percarbonate, sodium percarbamide, polyvinyl pyrrolidinone n $H_2O_2$ (n is a positive whole number greater than 0), urea peroxide and melamine peroxide. In the latter case, the addition compounds in the application mixture release hydrogen peroxide, which means that in addition to the addition compound, these agents contain free hydrogen peroxide in the cosmetic carrier. It is most particularly preferable for the hydrogen peroxide to be added to the agent as an aqueous hydrogen peroxide solution. The concentration of a hydrogen peroxide solution is determined by legal requirements and by the desired effect. 6 to 12 wt. % solutions in water are preferably used. Preferred agents contain, relative to their total weight, 0.01 to 12 wt. %, preferably 0.1 to 10 wt. %, particularly preferably 1 to 6 wt. %, of hydrogen peroxide (calculated as 100% $H_2O_2$).

Taking account of the aforementioned embodiments, a most specific and expressly preferred embodiment is one in which the agent for lightening keratin fibers contains in a cosmetic carrier (1) at least one compound chosen from 2-acetyl-1-methylpyridinium-p-toluenesulfonate, 2-acetyl-1-methylpyridinium benzenesulfonate, 2-acetyl-1-methylpyridinium bromide, 2-acetyl-1-methylpyridinium chloride, 2-acetyl-1-methylpyridinium hydrogen sulfate, 2-acetyl-1-methylpyridinium acetate, 2-acetyl-1-allylpyridinium-p-toluenesulfonate, 2-acetyl-1-allylpyridinium benzenesulfonate, 2-acetyl-1-allylpyridinium bromide, 2-acetyl-1-allylpyridinium chloride, 2-acetyl-1-allylpyridinium hydrogen sulfate, 2-acetyl-1-allylpyridinium acetate, 2,6-diacetyl-1-methylpyridinium-p-toluenesulfonate, 2,6-diacetyl-1-methylpyridinium benzenesulfonate, 2,6-diacetyl-1-methylpyridinium bromide, 2,6-diacetyl-1-methylpyridinium chloride, 2,6-diacetyl-1-methylpyridinium hydrogen sulfate and 2,6-diacetyl-1-methylpyridinium acetate, (2) an alkyl ether sulfate, particularly Sodium Coceth-30 sulfate, and (3) hydrogen peroxide.

A most particularly preferred lightening agent contains a combination of
 0.1 to 4.0 wt. % 2-acetyl-1-methylpyridinium-p-toluenesulfonate,
 0.1 to 3.0 wt. % Sodium Coceth-30 sulfate (active substance), and
 0.1 to 12.0 wt. % hydrogen peroxide.

It has been found that the bleaching capacity of the agents can be further increased if the lightening agents contain at least one aromatic, organic solvent. Aromatic solvents according to the invention are compounds having an aromatic structural unit such as a phenyl group in their structural formula and which are liquid under normal conditions (i.e., at room temperature and under normal pressure). They are preferably carbocyclic solvents which preferably additionally bear a hydroxyl group. Preferred examples of such aromatic solvents are alcohols such as benzyl alcohol, 2-phenylethyl alcohol, 1-phenylethyl alcohol, 2-phenoxyethanol, 3-methylbenzyl alcohol, 2-methoxybenzyl alcohol and 3-methoxybenzyl alcohol. A most particularly preferred aromatic solvent according to the invention is benzyl alcohol. Preferred agents contain at least one aromatic, organic solvent in an amount of 0.01 to 15 wt. %, particularly 0.1 to 10 wt. % and particularly preferably 0.5 to 5.0 wt. %, based on total weight of the ready-to-use agent.

Investigations in relation to this application have shown that the addition of an amino acid and/or an oligopeptide is capable of further increasing the lightening capacity of the bleaching agent. A further preferred embodiment is therefore an agent which additionally contains at least one amino acid and/or an oligopeptide.

Preferred amino acids and oligopeptides according to the invention are aliphatic amino acids and oligopeptides whose average isoelectric point (pI) is around 6. The isoelectric point is the pH of an aqueous solution at which the positive and negative charges of a substance containing differently charged groups (zwitterions) balance each other out. Examples of aliphatic amino acids are glycine (pI: 5.97), alanine (pI: 6.02), valine (pI: 5.96), leucine (pI: 5.98) or isoleucine (pI: 5.94).

Amino acids and oligopeptides can preferably be added to the agents in free form. In a number of cases, it is however advantageous to use the amino acids in their salt form. The agents most particularly preferably contain glycine and/or its physiologically acceptable salt as the amino acid.

Preferred agents contain amino acids and oligopeptides in an amount of 0.01 to 15 wt. %, particularly 0.1 to 10 wt. % and particularly preferably 0.5 to 5.0 wt. %, based on total weight of the ready-to-use agent.

Taking account of the aforementioned embodiments, a most specific and expressly preferred embodiment is one wherein the agent for lightening keratin fibers contains in a cosmetic carrier as the first component at least one compound chosen from 2-acetyl-1-methylpyridinium-p-toluenesulfonate, 2-acetyl-1-methylpyridinium benzenesulfonate, 2-acetyl-1-methylpyridinium bromide, 2-acetyl-1-methylpyridinium chloride, 2-acetyl-1-methylpyridinium hydrogen sulfate, 2-acetyl-1-methylpyridinium acetate, 2-acetyl-1-allylpyridinium-p-toluenesulfonate, 2-acetyl-1-allylpyridinium benzenesulfonate, 2-acetyl-1-allylpyridinium bromide, 2-acetyl-1-allylpyridinium chloride, 2-acetyl-1-allylpyridinium hydrogen sulfate, 2-acetyl-1-allylpyridinium acetate, 2,6-diacetyl-1-methylpyridinium-p-toluenesulfonate, 2,6-diacetyl-1-methylpyridinium benzenesulfonate, 2,6-diacetyl-1-methylpyridinium bromide, 2,6-diacetyl-1-methylpyridinium chloride, 2,6-diacetyl-1-methylpyridinium hydrogen sulfate and 2,6-diacetyl-1-methylpyridinium acetate, as the second component an alkyl ether sulfate, particularly Sodium Coceth-30 sulfate, and as the third component hydrogen peroxide, as well as additionally at least one compound chosen from glycine and benzyl alcohol.

Particularly preferred lightening agents contain a combination of
  0.1 to 4.0 wt. % 2-acetyl-1-methylpyridinium-p-toluenesulfonate,
  0.1 to 10 wt. % of at least one alkyl ether sulfate, particularly Sodium Coceth-30 sulfate,
  0.1 to 12.0 wt. % hydrogen peroxide, and
  0.1 to 3.0 wt. % benzyl alcohol.

Further particularly preferred lightening agents contain a combination of
  0.1 to 4.0 wt. % 2-acetyl-1-methylpyridinium-p-toluenesulfonate,
  0.1 to 10 wt. % of at least one alkyl ether sulfate, particularly Sodium Coceth-30 sulfate,
  0.1 to 12.0 wt. % hydrogen peroxide, and
  0.1 to 3.0 wt. % glycine.

Bleaching processes on keratin fibers typically take place in an alkaline environment. In order to protect the keratin fibers and skin as best as possible, it is not desirable to establish too high a pH. Therefore, the pH of the ready-to-use agent is preferably from 7 to 11, particularly 8 to 10.5. The pH values according to the present invention are pH values measured at a temperature of 22° C.

Alkalizing agents which can be used to establish the preferred pH can be chosen from ammonia, alkali metal hydroxides, alkanol amines, alkali metal metasilicates, alkali metal phosphates and alkali metal hydrogen phosphates. Lithium, sodium and potassium are preferably used as alkali metal ions.

Useful organic alkalizing agents are preferably chosen from alkanol amines from primary, secondary or tertiary amines having a $C_2$-$C_6$ alkyl parent substance bearing at least one hydroxyl group. Particularly preferred alkanol amines are chosen from 2-aminoethan-1-ol (monoethanolamine), 2-amino-2-methylpropan-1-ol, 2-amino-2-methylpropane-1,3-diol and triethanolamine. Particularly preferred alkanol amines are monoethanolamine and triethanolamine. Alkanol amines are preferably present in an amount from 0.05 to 10 wt. %, in particular 0.5 to 5 wt. %, based on total weight of the ready-to-use agent.

In the investigations relating to the present invention it has been found that preferred agents additionally contain an inorganic alkalizing agent. Inorganic alkalizing agent according to the invention are preferably chosen from sodium hydroxide, potassium hydroxide, calcium hydroxide, barium hydroxide, sodium phosphate, potassium phosphate, sodium silicate, potassium silicate, sodium carbonate and potassium carbonate, preferably from sodium hydroxide and potassium hydroxide.

The basic amino acids which can be used as alkalizing agents according to the invention are preferably chosen from L-arginine, D-arginine, D/L-arginine, L-lysine, D-lysine, D/L-lysine. L-arginine, D-arginine, D/L-arginine are particularly preferably used as an alkalizing agent.

As has already been mentioned, the agents can also be prepared directly before application from two or more separately packaged preparations. This allows for separation of incompatible ingredients to prevent a premature reaction. In order to avoid a premature, undesired reaction of the cationic 2-acylpyridinium derivatives of general formula (I) and the alkyl ether sulfate with the oxidizing agent, the 2-acylpyridinium derivatives and alkyl ether sulfate are conveniently packaged separately from the oxidizing agent and brought into contact only immediately before application. A conventional route thus involves mixing a first agent containing at least one cationic 2-acylpyridinium derivative of general formula (I) and at least one alkyl ether sulfate with a second agent containing the oxidizing agent(s) according to the invention immediately before use.

The present invention therefore also provides an agent for lightening keratin fibers, particularly human hair, which is obtained immediately before being applied to the hair from a free-flowing preparation (A) containing the cationic 2-acylpyridinium derivatives of the general formula (I) and an alkyl ether sulfate and an oxidizing agent preparation (B) containing at least one oxidizing agent chosen from hydrogen peroxide and/or its addition compounds with organic or inorganic compounds.

A further embodiment of the present invention is an agent for lightening keratin fibers, particularly human hair, which is obtained immediately before being applied to the hair from a free-flowing preparation (A) containing cationic 2-acylpyridinium derivatives of general formula (I) and an alkyl ether sulfate and an oxidizing agent preparation (B) containing at least one oxidizing agent chosen from hydrogen peroxide and/or its addition compounds with organic or inorganic compounds.

The oxidizing agent preparation (B) is preferably an aqueous, free-flowing oxidizing agent preparation. Preferred agents for lightening keratin fibers are those wherein the free-flowing oxidizing agent preparation (B) contains—relative to its weight—40 to 90 wt. %, preferably 50 to 85 wt. %, more preferably 55 to 80 wt. %, even more preferably 60 to 77.5 wt. %, and particularly 65 to 75 wt. % of water.

According to the invention, the oxidation coloring agent can also be applied to the hair together with a catalyst. Such catalysts include certain enzymes, iodides, quinones or metal ions. Suitable enzymes are, for example, peroxidases, which can significantly strengthen the action of small amounts of hydrogen peroxide. Particularly suitable catalysts for oxidation of the dye intermediates are the 2-electron oxidoreductases in combination with their specific substrates, for example, pyranose oxidase, glucose oxidase, glycerol oxidase, pyruvate oxidase, alcohol oxidase, lactate oxidase, tyrosinase oxidase, uricase, choline oxidase, amino acid oxidase. Use of certain metal ions or complexes can likewise be preferred in order to obtain improved bleaching actions. Suitable metal ions include $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$, $Ce^{4+}$, $V^{3+}$, $Co^{2+}$, $Ru^{3+}$ and $Al^{3+}$, particularly $Zn^{2+}$, $Cu^{2+}$ and $Mn^{2+}$. Particularly preferred agents contain these metal ions in an amount from 0.0001 to 2.5 wt. %, preferably 0.001 to 1 wt. %, based on total weight of the agent.

It has furthermore proved advantageous for the oxidizing agent preparations (B) to contain at least one stabilizer or complexing agent. Particularly preferred stabilizers are phenacetin, alkali benzoates (sodium benzoate) and salicylic acid.

Also preferred according to the invention is the use of complexing agents. Complexing agents are substances which are capable of complexing metal ions. Preferred complexing agents are chelating agents, in other words, substances which form cyclic compounds with metal ions, wherein an individual ligand occupies more than one coordination site on a central atom (i.e., it is at least "bidentate"). The number of bonded ligands depends on the coordination number of the central ion. Common preferred chelating agents are, for example, polyoxycarboxylic acids, polyamines, ethylenediaminetetraacetic acid (EDTA), nitrilotriacetic acid (NTA) and hydroxyethane diphosphonic acids or the alkali salts thereof. Preferred complexing agents are nitrogen-containing polycarboxylic acids, particularly EDTA, and phosphonates, preferably hydroxyalkane or aminoalkane phosphonates, and particularly 1-hydroxyethane-1,1-diphosphonate (HEDP) or the disodium or tetrasodium salt thereof and/or ethylenediamine tetramethylene phosphonate (EDTMP) or the hexasodium salt thereof and/or diethylenetriamine pentamethylene phosphonate (DTPMP) or the heptasodium or octasodium salt thereof.

In addition to the actual oxidizing agent, the oxidizing agent preparation contains further auxiliary substances and additives. It has thus proved preferable for the oxidizing agent preparation to contain at least one thickening agent. There are no restrictions in general regarding these thickening agents. Both organic and purely inorganic thickening agents can be used.

According to a first preferred embodiment the thickening agent is an anionic, synthetic polymer, such as are commercially obtainable, for example, under the trademarks Carbopol®, Rheothik® 11-80, Aculyn® 22, Aculyn® 33, Structure® 2001, Structure® 3001, Sepigel® 305, Simulgel® 600, Stabileze® QM, Latekoll® D.

According to a further embodiment, the thickening agent is a cationic synthetic polymer. A particularly suitable homopolymer is Polyquaternium-37, as well as polymers sold under the trade names Salcare® SC 92, Salcare® SC 95, Salcare® SC 96, Jaguar® HP8, Jaguar® HP60, Jaguar® HP120, Jaguar® DC 293 and Jaguar® HP105.

Furthermore, suitable natural thickening agents are known from the prior art. Such preferred natural thickening agents include biosaccharide gums of microbial origin, such as scleroglucan gums or xanthan gums, gums from plant exudates, such as gum arabic, ghatti gum, karaya gum, tragacanth gum, carrageen gum, agar-agar, carob seed meal, pectins, alginates, starch fractions and derivatives such as amylose, amylopectin and dextrins, cellulose derivatives, such as methyl cellulose, carboxyalkyl celluloses and hydroxyalkyl celluloses (Cellosize®, Natrosol®, Blanose®, Aquasorb®, Ambergum® and Cellgon®).

However, non-ionic, fully synthetic polymers such as polyvinyl alcohol or polyvinyl pyrrolidinone can also be used as thickening agents.

Layered silicates (polymeric crystalline sodium disilicates) have proved to be particularly suitable as inorganic thickening agents. Clays, particularly magnesium aluminum silicates such as bentonite, particularly smectites, such as montmorillonite or hectorite, which can optionally also be suitably modified, and synthetic layered silicates, such as the magnesium layered silicate sold by &id Chemie under the trade name Optigel®, are preferred in particular.

To further increase the lightening capacity, at least one optionally hydrated $SiO_2$ compound can additionally be added to the composition. Although even small amounts of the optionally hydrated $SiO_2$ compounds increase the lightening capacity, it can be preferable to use hydrated $SiO_2$ compounds in amounts from 0.05 wt. % to 15 wt. %, particularly preferably from 0.15 wt. % to 10 wt. % and most particularly preferably from 0.2 wt. % to 5 wt. %, based on the anhydrous composition according to the invention. The specified amounts indicate the content of $SiO_2$ compounds (excluding their water component) in the agents.

The present invention is not subject in general to restrictions regarding the optionally hydrated $SiO_2$ compounds. Silicic acids, oligomers and polymers thereof as well as salts thereof are preferred. Preferred salts are alkali salts, particularly potassium and sodium salts. Sodium salts are most particularly preferred. The optionally hydrated $SiO_2$ compounds can be present in various forms. According to the invention, $SiO_2$ compounds are preferably used in the form of silica gels or particularly preferably as water glass. In some cases these $SiO_2$ compounds can be present in aqueous solution. Water glasses that are particularly preferred are sold inter alfa by Henkel under the names Ferrosil® 119, soda water glass 40/42, Portil® A, Portil® AW and Portil® W and by Akzo under the name Britesil® C20.

Oxidizing agent preparation (B) and preparation (A) are preferably made up as free-flowing preparations.

An emulsifier or surfactant is furthermore preferably added to the free-flowing preparations (A) and/or (B). Surface-active substances are referred to as surfactants or as emulsifiers depending on their application area and are selected from anionic, cationic, zwitterionic, amphoteric and non-ionic surfactants and emulsifiers. These substances are described in detail below.

All anionic surface-active substances suitable for use on the human body are suitable as anionic surfactants in preparations according to the invention. These have a water-solubilizing anionic group such as a carboxylate, sulfate, sulfonate or phosphate group and a lipophilic alkyl group having approximately 8 to 30 C atoms. The molecule can additionally contain glycol or polyglycol ether groups, ester, ether and amide groups and hydroxyl groups. Examples of suitable anionic surfactants, each in the form of the sodium, potassium and ammonium salts as well as the mono-, di- and trialkanolammonium salts, are linear and branched fatty acids (soaps); ether carboxylic acids; acyl sarcosides; acyl taurides; acyl isethionates; sulfosuccinic acid mono- and -dialkyl esters and sulfosuccinic acid monoalkyl polyoxyethyl esters; linear alkane sulfonates; linear α-olefin sulfonates; sulfonates of unsaturated fatty acids; α-sulfofatty acid methyl esters; alkyl sulfates; mixtures of surface-active hydroxy sulfonates; sulfated hydroxyalkyl polyethylene and/or hydroxyalkylene propylene glycol ethers; esters of tartaric acid and citric acid with addition products of ethylene oxide and/or propylene oxide with fatty alcohols; alkyl- and/or alkenyl ether phosphates; sulfated fatty acid alkylene glycol esters; monoglyceride sulfates and monoglyceride ether sulfates.

Preferred anionic surfactants are alkyl sulfates and ether carboxylic acids with 10 to 18 C atoms in the alkyl group and up to 12 glycol ether groups in the molecule.

Surface-active compounds classified as zwitterionic surfactants are those bearing at least one quaternary ammonium group and at least one carboxylate, sulfonate or sulfate group in the molecule. Particularly suitable zwitterionic surfactants are betaines such as N-alkyl-N,N-dimethylammonium glycinates and 2-alkyl-3-carboxymethyl-3-hydroxyethyl imidazolines each having 8 to 18 C atoms in the alkyl or acyl group, as well as cocoacylaminoethyl hydroxyethyl carboxymethyl glycinate. A preferred zwitterionic surfactant is the fatty acid amide derivative known under the INCI name Cocamidopropyl Betaine.

Amphoteric surfactants are surface-active compounds which, in addition to a $C_8$-$C_{24}$ alkyl or $C_8$-$C_{24}$ acyl group, contain at least one free amino group and at least one COOH or $SO_3H$ group in the molecule and are capable of forming internal salts. Examples of suitable amphoteric surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids, each having approximately 8 to 24 C atoms in the alkyl group. Particularly preferred amphoteric surfactants are N-cocoalkyl aminopropionate, cocoacylaminoethyl aminopropionate and acyl sarcosine.

It has also proved advantageous for coloring and lightening agents according to the invention to contain non-ionogenic interfacially-active substances. Non-ionic surfactants contain as a hydrophilic group a polyol group, a polyalkylene glycol ether group or a combination of a polyol and polyglycol ether group, for example. Such compounds include addition products of ethylene oxide and/or with linear and branched fatty alcohols, fatty acids and alkyl phenols having 8 to 15 C atoms, addition products with linear and branched fatty alcohols, fatty acids and alkyl phenols end-capped with a methyl or $C_2$-$C_6$ alkyl residue; polyglycerol esters (such as the commercial products Lameform® TG1 and Dehymuls® PGPH (Henkel)); polyol fatty acid esters (such as the commercial products Hydagen® HSP or Sovermol types (Cognis)); more highly alkoxylated, preferably propoxylated and in particular ethoxylated mono-, di- and triglycerides; amine oxides; sorbitan fatty acid esters and their addition products of ethylene oxide (such as polysorbates); sugar fatty acid esters and their addition products; addition products of ethylene oxide with fatty acid alkanol amides and fatty amines; fatty acid-N-alkyl glucamides and alkyl polyglycosides.

In particular, $C_8$ to $C_{22}$ alkyl mono- and oligoglycosides and ethoxylated analogs thereof are suitable as non-ionic surfactants. Alkylene oxide addition products with saturated linear fatty alcohols and fatty acids containing 2 to 30 mol of ethylene oxide per mol of fatty alcohol or fatty acid are further preferred non-ionic surfactants. Preparations having outstanding properties are likewise obtained if they contain fatty acid esters of ethoxylated glycerol as non-ionic surfactants.

Additional anionic, non-ionic, zwitterionic or amphoteric surfactants are used in amounts from 0.1 to 45 wt. %, preferably 1 to 30 wt. % and most particularly preferably 1 to 15 wt. %, base on total amount of the ready-to-use agent.

Likewise preferred according to the invention are cationic surfactants of the quaternary ammonium compound, esterquat and amidoamine type. Preferred quaternary ammonium compounds are ammonium halides, particularly chlorides and bromides such as alkyltrimethylammonium chlorides, dialkyldimethylammonium chlorides and trialkylmethylammonium chlorides, for example cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, as well as imidazolium compounds known under the INCI names Quaternium-27 and Quaternium-83. Long alkyl chains of the aforementioned surfactants preferably have 10 to 18 carbon atoms. Other cationic surfactants which can be used are the quaternized protein hydrolysates. Alkylamidoamines are typically produced by amidation of natural or synthetic fatty acids and fatty acid cuts with dialkyl amino amines and, in addition to a good conditioning effect, have good biodegradability. A compound from this group of substances that is particularly suitable is the stearamidopropyl dimethylamine commercially available under the name Tegoamid® S 18. Esterquats are known substances containing both at least one ester function and at least one quaternary ammonium group as a structural element. Preferred esterquats are quaternized ester salts of fatty acids with triethanolamine, quaternized ester salts of fatty acids with diethanol alkyl amines and quaternized ester salts of fatty acids with 1,2-dihydroxypropyl dialkylamines (such as the commercial products Stepantex®, Dehyquart® and Armocare®). Cationic surfactants are present in agents according to the invention preferably in amounts of 0.05 to 10 wt. %, based on total agent. Amounts of 0.1 to 5 wt. % are particularly preferred.

In a preferred embodiment non-ionic, zwitterionic and/or amphoteric surfactants and mixtures thereof can be used.

For intense lightening of very dark hair, use of hydrogen peroxide or its addition products with organic or inorganic compounds alone is often not sufficient. In these cases a combination of hydrogen peroxide and persulfates or peroxodisulfates is generally used. It has been found that admixing 2-acylpyridinium derivatives according to the invention of general structure (I) and at least one alkyl ether sulfate results in an increase in the lightening capacity, not only with hydrogen peroxide alone but also with a combination of hydrogen peroxide and persulfate salts or peroxodisulfate salts.

Should the consumer desire a very strong bleaching effect, at least one inorganic persulfate salt or peroxodisulfate salt can be additionally included in the agent for lightening keratin fibers in addition to cationic 2-acylpyridinium compound of general structure (I), an alkyl ether sulfate and hydrogen peroxide. Preferred peroxodisulfate salts are ammonium peroxodisulfate, potassium peroxodisulfate and sodium peroxodisulfate. The peroxodisulfate salts can be present in an amount from 0.1 to 25 wt. %, particularly from 0.5 to 15 wt. %, based on total weight of the ready-to-use agent.

Use of persulfate salts or peroxodisulfate salts generally takes place in the form of an optionally dedusted powder or a pressed molding. To prevent premature degradation of the 2-acylpyridinium derivatives through contact with the persulfates or peroxodisulfates, it is preferable to provide the persulfates or peroxodisulfates as a separately packaged component (C).

In this connection, the present invention also provides an agent for lightening human hair containing at least three components. This agent is prepared immediately before being applied to the hair by the careful mixing of a free-flowing preparation (A) containing cationic 2-acylpyridinium derivatives of general formula (I) and at least one alkyl ether sulfate, an oxidizing agent preparation (B) containing at least one oxidizing agent chosen from hydrogen peroxide and/or its addition compounds with organic or inorganic compounds, and additionally a third preparation (C) in powder form containing at least one inorganic persulfate salt or peroxodisulfate salt.

It is likewise possible to package the alkyl ether sulfate together with the oxidizing agent. A further embodiment of the present invention is therefore an agent which is prepared immediately before being applied to the hair by careful mixing of a free-flowing preparation (A) containing cationic 2-acylpyridinium derivatives of general formula (I), an oxidizing agent preparation (B) containing at least one alkyl ether sulfate and at least one oxidizing agent chosen from hydrogen peroxide and/or its addition compounds with organic or inorganic compounds, and additionally a third preparation (C) in powder form containing at least one inorganic persulfate salt or peroxodisulfate salt.

Mixing preparations (A) and (B) or optionally preparations (A), (B) and (C) before application leads to an application mixture which is an agent according to the invention containing the three constituents.

In the context of this invention compounds which under perhydrolysis conditions give rise to aliphatic peroxocarboxylic acids and/or substituted perbenzoic acid, carbonic acid derivatives, alkyl carbonates and carbamates as well as silyl carbonates and carbamates can be used as additional bleaching strength intensifiers. At least one compound chosen from acetic acid, lactic acid, tartaric acid, citric acid, salicylic acid and ortho-phthalic acid can preferably be included in the compositions as further additional bleach intensifiers. Bleaching strength intensifiers used in addition to or instead of peroxo compounds are included in the cosmetic agents preferably in amounts from 0.05 to 10 wt. %, particularly in amounts from 0.2 to 5 wt. %, based on total weight of the ready-to-use agent.

Although there are generally no restrictions regarding the formulation of the bleaching preparation (C), it is preferable if preparation (C) is formulated to be free from water. Free from water according to the present invention means a water content relative to preparation (C) of 5 wt. % or less, particularly 2 wt. % or less. Bleaching preparations containing 0.1 wt. % or less of water can be particularly preferred. Preparation (C) is preferably formulated as a powder or as an anhydrous paste. When formulated as an anhydrous paste, it has proven particularly preferable for preparation (C) to contain at least one non-hydroxylated fatty acid ester with a melting point of 50° C. or less, particularly 30° C. or less, and/or at least one $C_{10}$-$C_{30}$ fatty acid with at least one additional hydroxyl group and/or a derivative thereof.

Agents according to the invention can be provided not only as pure lightening agents (i.e., as bleaching agents), but also as coloring and lightening agents which color the keratin fibers at the same time as lightening them.

The agents can therefore additionally also contain dyes and/or dye intermediates and can thus be provided as agents having a simultaneous lightening and coloring action. Such agents are described below as "coloring agents", as "lightening coloring agents" or as "coloring and lightening agents". One skilled in the art is familiar with various coloring systems for the provision of color-changing cosmetic agents, particularly for skin or keratin-containing fibers such as human hair, depending on the requirements of the coloring process.

In one embodiment for color change the subject-matter of the present invention can be combined with at least one color-changing component. Color-changing components within the meaning of the present invention are preferably chosen from (1) at least one oxidation dye intermediate and/or (2) at least one direct dye and/or (3) at least one precursor of nature-analogous dyes.

Preferred agents for coloring and/or lightening keratin fibers thus contain at least one oxidation dye intermediate of the developer type and/or coupler type.

Preferred developer components are chosen from at least one compound from p-phenylenediamine, p-toluoylenediamine, 2-(2-hydroxyethyl)-p-phenylenediamine, dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, and the physiologically acceptable salts of these compounds. Particularly preferred developer components here are p-toluoylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole and the physiologically acceptable salts thereof. The developer components are preferably used in an amount from 0.005 to 20 wt. %, preferably 0.1 to 5 wt. %, relative in each case to the ready-to-use oxidation coloring agent.

Concerning oxidative dyeing, coupler components develop no significant color on their own but always need the presence of developer components. It is therefore preferable that, with the use of at least one coupler component, at least one developer component is additionally used.

Preferred coupler components are chosen from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically acceptable salts of the aforementioned compounds. Resorcinol, 2-methylresorcinol, 5-amino-2-methylphenol, 3-aminophenol, 2-(2,4-diaminophenoxy)ethanol, 1,3-bis(2,4-diaminophenoxy)propane, 1-methoxy-2-amino-4-(2'-hydroxyethylamino)benzene, 2-amino-3-hydroxypyridine and 1-naphthol and one of the physiologically acceptable salts thereof are most particularly preferred. The coupler components are preferably used in an amount from 0.005 to 20 wt. %, preferably 0.1 to 5 wt. %, based on total ready-to-use oxidation coloring agent.

The agents can further contain at least one direct dye. These are dyes which attach directly to the hair and require no oxidative process to develop the color. Direct dyes are typically nitrophenylene diamines, nitroaminophenols, azo dyes, anthraquinones or indophenols. Direct dyes are preferably used in an amount from 0.001 to 20 wt. %, based on complete application preparation. The total amount of direct dyes is preferably at most 20 wt. %. Direct dyes can be divided into anionic, cationic and non-ionic direct dyes.

Suitable anionic direct dyes include FD&C Yellow No. 6, Acid Yellow 1, Acid Yellow 3, Acid Yellow 9, Acid Yellow 23, Acid Yellow 36, Acid Yellow 73, Acid Orange 3, Acid Orange 6, Acid Orange 7, Acid Orange 24, Acid Red 4, Acid Red 14, Acid Red 18, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Pigment Red 57:1, FD&C Red No. 4, Acid Green 25, Acid Green 50, Acid Blue 1, Acid Blue 3, Acid Blue 7, Acid Blue 9, Acid Blue 25, Acid Blue 62, Acid Blue 74, Acid Violet 9, Acid Violet 43, Acid Brown 13, Acid Black 1, Acid Black 52, Food Black No. 1,3',3",5',5"-tetrabromophenolsulfonphthalein (bromophenol blue). Preferred anionic direct dyes are the compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Suitable cationic direct dyes are Basic Blue 6, Basic Blue 7, Basic Blue 8, Basic Blue 9, Basic Blue 26, Basic Blue 41, Basic Blue No. 99, Basic Violet 1, Basic Violet 2, Basic Violet 3, Basic Violet 10, Basic Violet 14, Basic Brown 4, Basic Brown 16, 1-[(4-Amino-2-nitrophenyl)azo]-7-(trimethylammonio)-2-naphthol chloride, Basic Brown 17, Basic Orange 69, Basic Red 2, Basic Red 22, Basic Red 76, Basic Yellow 2, Basic Yellow 11, Basic Yellow 57, Basic Green 1, Basic Green 4,1-(2-morpholinium propylamino)-4-hydroxy-9,10-anthraquinone methylsulfate, 1-[(3-(dimethyl propylaminium) propyl)amino]-4-(methylamino)-9,10-anthraquinone chloride and direct dyes containing a heterocyclic compound having at least one quaternary nitrogen atom. Preferred cationic direct dyes are cationic triphenylmethane dyes, such as Basic Blue 7, Basic Blue 26, Basic Violet 2 and Basic Violet 14, aromatic systems substituted with a quaternary nitrogen group, such as Basic Yellow 57, Basic Red 76, Basic Blue 99, Basic Brown 16 and Basic Brown 17, as well as direct dyes containing a heterocyclic compound having at least one quaternary nitrogen atom, such as are cited in EP-A2-998 908, to which reference is explicitly made to claims 6 to 11. Compounds also known under the names Basic Yellow 87, Basic Orange 31 and Basic Red 51 are most particularly preferred cationic direct dyes. Cationic direct dyes sold under the trademark Arianor® are particularly preferred cationic direct dyes according to the invention.

Non-ionic nitro and quinone dyes and neutral azo dyes in particular are suitable as non-ionic direct dyes. Preferred non-ionic direct dyes are compounds known under the international names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl) amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

It is not necessary for the direct dyes to be uniform compounds. Instead, it is possible for the individual dyes to also contain small amounts of additional components arising from the manufacturing processes for the individual dyes, provided that they do not adversely influence the coloring result or need to be excluded for other, for example, toxicological, reasons. Naturally occurring dyes, such as are present in henna red, henna neutral, henna black, chamomile flowers, sandalwood, black tea, alder buckthorn bark, sage, logwood, madder root, catechu and alkanet root, can also be used as direct dyes.

Indoles and indolines containing at least two groups chosen from hydroxyl and/or amino groups, preferably as a substituent on the six-membered ring, are preferably used as dye precursors of nature-analogous dyes. These groups can bear further substituents, for example in the form of an etherification or esterification of the hydroxyl group or an alkylation of the amino group. In a further embodiment, the coloring agents contain at least one indole and/or indoline derivative. Compositions according to the invention containing precursors of nature-analogous dyes are preferably used as air-oxidative coloring agents. In this embodiment the compositions are therefore not mixed with an additional oxidizing agent. Dye precursors of nature-analogous dyes are preferably used in an amount from 0.001 to 5 wt. %, based on complete application preparation. The total amount of direct dyes is preferably at most 3 wt. %. Particularly preferred indoline derivatives are 5,6-dihydroxyindoline, N-methyl-5, 6-dihydroxyindoline, N-ethyl-5,6-dihydroxyindoline, N-propyl-5,6-dihydroxyindoline, N-butyl-5,6-dihydroxyindoline and 5,6-dihydroxyindoline-2-carboxylic acid, in particular 5,6-dihydroxyindoline. Particularly preferred indole derivatives are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole and 5,6-dihydroxyindole-2-carboxylic acid, in particular 5,6-dihydroxyindole.

The agents can additionally contain active ingredients, auxiliary substances and additives, such as non-ionic polymers (such as vinyl pyrrolidinone/vinyl acrylate copolymers, polyvinyl pyrrolidinone, vinyl pyrrolidinone/vinyl acetate copolymers, polyethylene glycols and polysiloxanes); silicones such as volatile or non-volatile, straight-chain, branched or cyclic, crosslinked or uncrosslinked polyalkylsiloxanes (such as dimethicone or cyclomethicone), polyarylsiloxanes and/or polyalkylarylsiloxanes, particularly polysiloxanes with organofunctional groups, such as amodimethicones, dimethicone copolyols, linear polysiloxane(A)-polyoxyalkylene(B) block copolymers, grafted silicone polymers (such as Abil B 8832 from Degussa); cationic polymers (such as quaternized cellulose ethers, polysiloxanes with quaternary group, dimethyl diallyl ammonium chloride polymers, acrylamide-dimethyl diallyl ammonium chloride copolymers, diethyl sulfate-quaternized dimethylaminoethyl methacrylate-vinyl pyrrolidinone copolymers, vinyl pyrrolidinone-imidazolinium methochloride copolymers and quaternized polyvinyl alcohol); zwitterionic and amphoteric polymers (such as acrylamidopropyl trimethyl ammonium chloride/acrylate copolymers and octylacrylamide/methyl methacrylate/tert-butylaminoethyl methacrylate/2-hydroxypropyl methacrylate copolymers, diallyl dimethyl ammonium chloride/acrylate copolymers, t-butylaminoethyl methacrylate/N-(1,1,3,3-tetramethylbutyl)acrylamide/acrylate(/methacrylate) copolymers); anionic polymers (such as polyacrylic acids, crosslinked polyacrylic acids, vinyl acetate/crotonic acid copolymers, vinyl pyrrolidinone/vinyl acrylate copolymers, vinyl acetate/butyl maleate/isobornyl acrylate copolymers, methyl vinyl ether/maleic anhydride copolymers and acrylic acid/ethyl acrylate/N-t-butylacrylamide terpolymers); other thickening agents such as agar-agar, guar gum, alginates, xanthan gum, gum arabic, karaya gum, carob seed meal, linseed gums, dextrans, cellulose derivatives, for example methyl cellulose, hydroxyalkyl cellulose and carboxymethyl cellulose, starch fractions and derivatives such as amylose, amylopectin and dextrins, clays such as bentonite or fully synthetic hydrocolloids such as for example polyvinyl alcohol; hair-conditioning compounds (such as phospholipids, soy lecithin, egg lecithin and cephalins, as well as silicone oils); protein hydrolysates (particularly elastin, collagen, keratin, milk protein, soy protein and wheat protein hydrolysates, condensation products thereof with fatty acids as well as quaternized protein hydrolysates); perfume oils, dimethyl isosorbide and cyclodextrin; active ingredients to improve the fiber structure (such as glucose, galactose, fructose, fruit sugars, lactose, maleic acid and lactic acid); defoaming agents such as silicones; dyes or pigments to color the agent; anti-dandruff active ingredients such as piroctone olamine, zinc omadine and climbazole; other amino acids and oligopeptides, particularly arginine and/or serine; light stabilizers (derivatized benzophenones, cinnamic acid derivatives and triazines); active ingredients such as panthenol, pantothenic acid, pantolactone, allantoin, pyrrolidinone carboxylic acids and salts thereof as well as bisabolol; polyphenols (in particular hydroxycinnamic acids, 6,7-dihydroxycoumarin, hydroxybenzoic acids, catechins, tannins, leukoanthocyanidins, anthocyanidins, flavanones, flavones and flavonols); ceramides, preferably sphingolipids such as Ceramide I, Ceramide II, Ceramide 1, Ceramide 2, Ceramide 3, Ceramide 5 and Ceramide 6, or pseudoceramides such as N—($C_8$-$C_{22}$ acyl) ($C_8$-$C_{22}$ acyl) hydroxyproline; vitamins, provitamins and vitamin precursors, in particular those of groups A, $B_3$, $B_5$, $B_6$, C, E, F and H; plant extracts; cholesterol; consistency modifiers such as sugar esters, polyol esters or polyol alkyl ethers; fats and waxes such as beeswax, montan wax and paraffins; fatty acid alkanol amides; swelling and penetrating substances such as glycerol, propylene glycol monoethyl ethers, carbonates, hydrogen carbonates, guanidines, ureas as well as primary, secondary and tertiary phosphates; opacifiers such as latex, styrene/PVP and styrene/acrylamide copolymers; pearlescent agents such as ethylene glycol mono- and distearate and PEG-3 distearate; blowing agents such as propane-butane mixtures, $N_2O$, dimethyl ether, $CO_2$ and air, as well as antioxidants.

One skilled in the art typically selects these substances according to the desired properties of the agents. Regarding further optional components and their amounts used, reference is made to the relevant manuals known to onde skilled in the art, for example Kh. Schrader, *Grundlagen and Rezepturen der Kosmetika*, $2^{nd}$ Ed., Htithig Buch Verlag, Heidelberg (1989). Additional active ingredients and auxiliary substances are used in the agents preferably in amounts of 0.0001 to 10 wt. %, particularly 0.0005 to 5 wt. %, based on total weight of the application mixture.

In some cases it has proven positive for increasing the lightening capacity if the agent contains ammonium compounds. As a further constituent, compositions according to the invention can therefore contain at least one ammonium compound from the group ammonium chloride, ammonium carbonate, ammonium bicarbonate, ammonium sulfate and/or ammonium carbamate. Ammonium compounds are preferably included in an amount from 0.5 to 10 wt. %, preferably 1 to 5 wt. %, based on overall composition of the agent.

The present invention also provides a method for lightening keratin fibers, particularly human hair, wherein an agent of the first subject-matter of the invention is applied to the keratin-containing fibers, left on the fiber for 5 to 60 minutes and then rinsed out again or washed out with a shampoo. The temperature during contact time of 5 to 60 minutes is preferably from 10° C. to 40° C., particularly from 20° C. to 38° C. A lightening method in which the compounds of general structure (I) and the alkyl ether sulfate are initially separate from the hydrogen peroxide is preferred.

The present invention therefore also provides a method for lightening human hair wherein a composition on an aqueous basis containing hydrogen peroxide or a solid addition compound of hydrogen peroxide with inorganic or organic compounds is mixed with a composition containing at least one 2-acylpyridinium derivative of the general structure (I) and at least one alkyl ether sulfate to form an agent of the first subject-matter of the invention, and this mixture is then applied to the hair.

A further embodiment of the method according to the invention for lightening human hair is directed towards mixing a composition on an aqueous basis containing hydrogen peroxide or a solid addition compound of hydrogen peroxide with inorganic or organic compounds with a further agent containing preferably at least one alkalizing agent and/or direct hair dye and/or at least one oxidation dye intermediate and an agent containing a 2-acylpyridinium derivative of general structure (I) and additionally an alkyl ether sulfate to form a homogenous composition, and applying this mixture to the hair.

In order to obtain a particularly intense lightening, a further embodiment of the present invention is finally a method wherein a composition on an aqueous basis containing hydrogen peroxide or a solid addition compound of hydrogen peroxide with inorganic or organic compounds is mixed with a composition containing at least 2-acylpyridinium derivative of general structure (I) and at least one alkyl ether sulfate together with a bleaching agent containing at least one bleaching strength intensifier to form an agent of the first subject-matter of the invention, and this is applied to the hair. The aforementioned restrictions and, with necessary alterations, all that has been stated regarding the agents according to the invention apply to the embodiments of the method according to the invention.

A preferred packaging format of the agent according to the invention is a kit of parts containing in separately made-up containers
- at least one oxidizing agent preparation (B) containing hydrogen peroxide or a solid addition compound of hydrogen peroxide with inorganic or organic compounds, and
- at least one preparation (A), wherein preparation (A) contains in a cosmetic carrier at least one 2-acylpyridinium derivative of the general structure (I) and at least one alkyl ether sulfate.

If a particularly strong lightening effect is desired, a preferred further packaging format of the agent is a kit of parts containing in separately made-up containers
- at least one oxidizing agent preparation (B) containing hydrogen peroxide or a solid addition compound of hydrogen peroxide with inorganic or organic compounds,
- at least one bleaching preparation (C) containing at least one bleaching strength intensifier, and at least one preparation (A), wherein preparation (A) contains in a cosmetic carrier at least one acylpyridinium derivative of the general structure (I) and at least one alkyl ether sulfate.

The multicomponent kit of parts preferably also contains instructions for use. It can moreover be preferable if an application aid such as a comb or a brush and/or personal protection equipment such as disposable gloves are included with the kit. All that has been stated regarding the agents applies with necessary alterations to further preferred embodiments of the multicomponent kit of parts.

The invention lastly provides for use of the agents of the first subject-matter of the invention for lightening keratin-containing fibers, particularly human hair.

All that has been stated regarding the agents applies with necessary alterations to further preferred embodiments of the use according to the invention.

EXAMPLES

1.0 Synthesis Example

1.1 Synthesis of 2-acetyl-1-methylpyridinium-p-toluenesulfonate

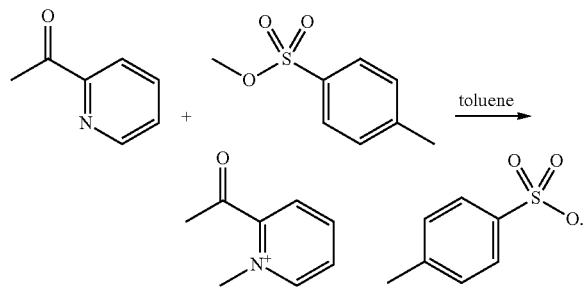

50.0 g (0.41 mol) of 2-acetylpyridine and 80.6 g (0.43 mol) of p-toluenesulfonic acid methyl ester were refluxed in 250 ml of toluene for 5 hours. After cooling, the light brown solid that had formed was filtered off, rinsed with toluene and dried under vacuum. Yield: 77.2 g (61%); $^1$H-NMR (400 MHz, DMSO-$d_6$): δ [ppm]=2.30 (s, 31-1); 2.81 (s, 3H); 4.35 (s, 3H); 7.10 (d, 2H); 7.47 (d, 2H); 8.26 (dd, 1H); 8.61 (d, 1H); 8.78 (dd, 1H); 9.18 (d, 1H).

2.0 Bleaching Examples 2.1 Bleaching with Hydrogen Peroxide—
2.1.1 Preparation of a Bleaching Cream:
Bleaching creams were prepared from the listed ingredients as follows:

| Raw material | wt. % | | |
|---|---|---|---|
| | C1 | C2 | E1 |
| Hydrenol D | 6.9 | 6.9 | 6.9 |
| Lorol tech. | 2.5 | 2.5 | 2.5 |
| Eumulgin B1 | 0.6 | 0.6 | 0.6 |
| Eumulgin B2 | 0.6 | 0.6 | 0.6 |
| Akypo Soft 45 NV | 10.0 | 10.0 | 10.0 |
| Plantacare 1200 UP | 2.0 | 2.0 | 2.0 |
| Texapon K 14 S 70 C | 2.8 | 2.8 | 2.8 |

-continued

| Raw material | wt. % | | |
|---|---|---|---|
| | C1 | C2 | E1 |
| Ammonium sulfate | 1.0 | 1.0 | 1.0 |
| Ascorbic acid | 0.1 | 0.1 | 0.1 |
| Sodium silicate 40/42 | 0.5 | 0.5 | 0.5 |
| Turpinal SL | 0.2 | 0.2 | 0.2 |
| Potassium hydroxide | 0.8 | 0.8 | 0.8 |
| Ammonia, 25 wt. % aqueous | 7.1 | 7.1 | 7.1 |
| 4-Acetyl-1-methylpyridinium-p-toluenesulfonate | — | 2.0 | — |
| 2-Acetyl-1-methylpyridinium-p-toluenesulfonate (Example 1.1) | — | — | 2.0 |
| Water | to 100 | to 100 | to 100 |

Raw materials used:

| | |
|---|---|
| Hydrenol ® D | $C_{16}$-$C_{18}$ fatty alcohol (INCI name: Cetearyl alcohol) (Cognis) |
| Lorol ® tech. | $C_{12}$-$C_{18}$ fatty alcohol (INCI name: Coconut alcohol) (Cognis) |
| Eumulgin ® B1 | $C_{16}$-$C_{18}$ fatty alcohol, ethoxylated (12 EO) (INCI name: Ceteareth-12) (Cognis) |
| Eumulgin ® B2 | $C_{16}$-$C_{18}$ fatty alcohol, ethoxylated (20 EO) (INCI name: Ceteareth-20) (Cognis) |
| Akypo ® Soft 45 NV | $C_{12}$-$C_{14}$ fatty alcohol ether acetic acid, sodium salt (4.5 EO) (INCI name: Sodium Laureth-5 Carboxylate) (KAO Chemicals) |
| Plantacare ® 1200 UP | $C_{12}$-$C_{16}$ fatty alcohol glucoside (INCI name: Lauryl Glucoside) (Cognis) |
| Texapon ® K 14 S 70 C | Myristyl ether sulfate, sodium salt (approx. 70% active substance; INCI name: Sodium Myreth Sulfate) (Cognis) |
| Turpinal ® SL | 1-Hydroxyethane-1,1-diphosphonic acid (approx. 60% active substance content; INCI name: Etidronic Acid, Aqua (Water)) (Solutia) |
| Sodium silicate 40/42 | Sodium silicate |

Hydrenol D, Lorol, Eumulgin B1, Eumulgin B2, Akypo Soft 45 NV, Plantacare 1200 UP and Texapon K 14 S 70 C were melted together at 80° C. and dispersed with part of the water. The remaining formulation ingredients were then incorporated in sequence while stirring. The mixture was then made up with water to 100 wt. % and the formulation stirred until cold. Formulations C1 and C2 are comparison formulations not according to the invention, with neither containing 2-acylpyridinium derivative and C2 containing 4-acylpyridinium derivative. Formulation E1 is an example according to the invention containing the bleach activator 2-acetyl-1-methylpyridinium-p-toluenesulfonate.

2.1.2 Mixing with the Developer Dispersion:

Each bleaching cream was mixed in a ratio of 1:1 with a developer dispersion having a composition as follows. The pH of the application mixture was from 9 to 10.2.

| Raw material | wt. % |
|---|---|
| Ammonia 25% | 0.62 |
| Dipicolinic acid | 0.10 |
| Disodium pyrophosphate | 0.03 |
| Turpinal SL | 1.50 |
| Texapon NSO | 2.00 |
| Dow Corning DB 110 A | 0.07 |
| Aculyn 33 A | 12.00 |
| Hydrogen peroxide, 50 wt. %, aqueous | 22.40 |
| Water | to 100 |

| | |
|---|---|
| Texapon ® NSO | Lauryl ether sulfate, sodium salt (approx. 27.5% active substance; INCI name: Sodium Laureth Sulfate) (Cognis) |
| Aculyn ® 33 | Acrylic polymer (approx. 28% solids in water; INCI name: Acrylates Copolymer) (Rohm & Haas) |
| Dow Corning ® DB 110 A | Non-ionic silicone emulsion (INCI name: Dimethicone) (Dow Corning) |

For the bleaching process, 4 times the amount of final application mixture was applied to strands of dark blonde hair (code Kerling 7/0) and light brown hair (code Fischbach & Miller 6923) weighing approx. 0.7 g. After the strands had been bleached for 30 minutes at 32° C. they were washed with a commercial shampoo and dried with a hairdryer.

2.1.3 Assessment of the Lightening Capacity:

Each hair strand was measured by colorimetry before and after the bleaching process. The dL value calculated using the following formula was used as a measure of the lightening capacity of each formulation:

$$\Delta L = L_{after} - L_{before}$$

$L_{after}$=brightness of the strands after bleaching
$L_{before}$=brightness of the strands before bleaching Twelve measurements were performed for each formulation and each hair type, and the average was calculated from the individual values in each case. The higher the dL value, the better the lightening capacity of the individual formulation.

Lightening Capacity on Dark Blonde Strands (Kerling 7/0)—

| dL (C1) | dL (C2) | dL (E1) |
|---|---|---|
| 9.5 | 12.0 | 13.6 |

Lightening Capacity on Light Brown Strands (Fischbach & Miller 6923)—

| dL (C1) | dL (C2) | dL (E1) |
|---|---|---|
| 10.3 | 11.6 | 13.0 |

2.1.4 Significance of the Results:

The bleaching actions of the various formulations can be estimated by comparing the dL values. A comparison of the results shows that by adding the bleach activator according to the invention to the bleaching formulation, higher ΔL values can be obtained, increasing the lightening effects beyond the extent known from the prior art.

2.2 Bleaching with Hydrogen Peroxide and Benzyl Alcohol or Sodium Coceth-30 Sulfate—

2.2.1 Preparation of a Bleaching Cream:

Bleaching creams were prepared from the listed constituents as follows:

| | wt. % | | | |
|---|---|---|---|---|
| Raw material | C3 | E2 | E3 | E4 |
| Hydrenol D | 6.9 | 6.9 | 6.9 | 6.9 |
| Lorol tech. | 2.5 | 2.5 | 2.5 | 2.5 |
| Eumulgin B1 | 0.6 | 0.6 | 0.6 | 0.6 |
| Eumulgin B2 | 0.6 | 0.6 | 0.6 | 0.6 |
| Akypo Soft 45 NV | 10.0 | 10.0 | 10.0 | 10.0 |
| Plantacare 1200 UP | 2.0 | 2.0 | 2.0 | 2.0 |
| Texapon K 14 S 70 C | 2.8 | 2.8 | 2.8 | 2.8 |
| Ammonium sulfate | 1.0 | 1.0 | 1.0 | 1.0 |
| Ascorbic acid | 0.1 | 0.1 | 0.1 | 0.1 |
| Sodium silicate 40/42 | 0.5 | 0.5 | 0.5 | 0.5 |
| Turpinal SL | 0.2 | 0.2 | 0.2 | 0.2 |
| Potassium hydroxide | 0.8 | 0.8 | 0.8 | 0.8 |
| Ammonia, 25 wt. % aqueous | 7.1 | 7.1 | 7.1 | 7.1 |
| Benzyl alcohol | — | — | 2.0 | — |
| Disponil FES 77 (active substance) | — | — | — | 2.0 |
| 2-Acetyl-1-methylpyridinium-p-toluenesulfonate (according to Example 1.1) | — | 2.0 | 2.0 | 2.0 |
| Water | to 100 | to 100 | to 100 | to 100 |

Disponil® FES 77 $C_{12}$-$C_{18}$ fatty alcohol ether sulfate, sodium salt (30 EO) (approx. 31-33% active substance in water; INCI name: Sodium Coceth-30 Sulfate) (Cognis)

In a manner analogous to Example 2.1, Hydrenol D, Lorol, Eumulgin B1, Eumulgin B2, Akypo Soft 45 NV, Plantacare 1200 UP and Texapon K 14 S 70 C were melted together at 80° C. and dispersed with part of the water. The remaining formulation ingredients were then incorporated in sequence while stirring. The mixture was then made up with water to 100 wt. % and the formulation stirred until cold. Formulation C3 is a comparison formulation not according to the invention without bleach activator. Formulations E2, E3 and E4 are examples according to the invention.

2.2.2 Mixing with the Developer Dispersion:

Each bleaching cream was mixed in a ratio of 1:1 with a developer dispersion according to Example 2.1. The pH of the final application mixture was from 9 to 10.2. For the bleaching process, 4 times the amount of the final application mixture was applied to strands of dark blonde hair (code Kerling 7/0), light brown hair (code Fischbach & Miller 6923) and dark brown hair (code Kerling 2/0) weighing approx. 0.7 g. Hair from a single batch was used in each case for all measurements in a series. After the strands had been bleached for 30 minutes at 32° C. they were washed with a commercial shampoo and dried with a hairdryer.

2.2.3 Assessment of the Lightening Capacity:

Twelve measurements were performed by colorimetry in an analogous manner to Example 2.1 for each formulation and each hair type, and the average was calculated from the individual values in each case. The higher the dL value, the better the lightening capacity of the individual formulation.

Lightening Capacity on Dark Blonde Strands (Kerling 7/0)—

| dL (C3) | dL (E2) | dL (E3) | dL (E4) |
|---|---|---|---|
| 11.47 | 13.94 | 14.48 | 14.54 |

Lightening Capacity on Light Brown Strands (Fischbach & Miller 6923)—

| dL (C3) | dL (E2) | dL (E3) | dL (E4) |
|---|---|---|---|
| 10.01 | 12.10 | 14.09 | 12.34 |

Lightening Capacity on Dark Brown Strands (Kerling 2/0)—

| dL (C3) | dL (E1) | dL (E2) | dL (E3) |
|---------|---------|---------|---------|
| 4.77    | 6.87    | 8.32    | 7.10    |

2.2.4 Significance of the Results:

Bleaching actions of the various formulations can be seen by comparing the dL values. It is clearly apparent that higher dL values and hence a better lightening effect can be achieved with the combination according to the invention of hydrogen peroxide, a co-activator and the cationic 2-acylpyridinium derivative than is possible with the use of the 2-acylpyridinium derivative alone.

We claim:

1. Agent for lightening keratin fibers comprising, in a cosmetic carrier:
   (i) at least one cationic 2-acylpyridinium derivative according to formula (I)

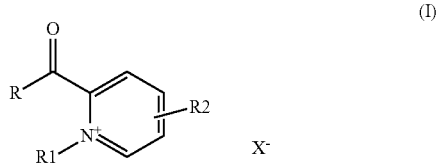

wherein
   R is a $C_1$-$C_4$ alkyl group, a $C_2$-$C_6$ hydroxyalkyl group or a $C_1$-$C_6$ alkoxy $C_2$-$C_6$ alkyl group,
   R1 is a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_1$-$C_6$ alkyl group, an aryl $C_1$-$C_6$ alkyl group, a heteroaryl $C_1$-$C_6$ alkyl group, a mono- or di-($C_1$-$C_6$ alkyl)amino $C_2$-$C_6$ alkyl group, a 3-oxobutyl group, a 2-oxopropyl group, an aryl group or a heteroaryl group,
   R2 is hydrogen, a halogen, a nitrile group, a nitro group, an amino group, a mono-$C_1$-$C_6$-alkylamino group, a di-($C_1$-$C_6$-alkylamino group, a hydroxyl group, a $C_1$-$C_6$ alkoxy group, a $C_1$-$C_6$ alkyl group, a partially or completely halogenated $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a $C_1$-$C_6$ alkoxycarbonyl group, a carboxyl group, a carbamoyl group or an acyl group R'C(O), in which R' denotes a $C_1$-$C_4$ alkyl group, a $C_2$-$C_6$ hydroxyalkyl group or a $C_1$-$C_6$ alkoxy $C_2$-$C_6$ alkyl group,
   $X^-$ is a physiologically acceptable anion,
   (ii) at least one anionic surfactant chosen from alkyl ether sulfates according to formula (II)

R''—(OCH$_2$CH$_2$)$_n$—OSO$_3$M, wherein R'' is a linear or branched, saturated or optionally unsaturated $C_8$-$C_{30}$ alkyl chain, n is a number greater than 2 and M is hydrogen or a physiologically acceptable cation, and
   (iii) hydrogen peroxide or a solid addition compound of hydrogen peroxide with inorganic or organic compounds.

2. Agent according to claim 1, wherein R1 is a $C_1$-$C_6$ alkyl group, a $C_2$-$C_6$ alkenyl group or a $C_2$-$C_6$ hydroxyalkyl group.

3. Agent according to claim 1, wherein R2 is hydrogen, a $C_1$-$C_6$ alkyl group or an acyl group R'C(O), wherein R' is a $C_1$-$C_4$ alkyl group.

4. Agent according to claim 1, wherein the at least one cationic 2-acylpyridinium derivative of formula (I) is at least 2-acetyl-1-methylpyridinium-p-toluenesulfonate, 2-acetyl-1-methylpyridinium benzenesulfonate, 2-acetyl-1-methylpyridinium bromide, 2-acetyl-1-methylpyridinium chloride, 2-acetyl-1-methylpyridinium hydrogen sulfate, 2-acetyl-1-methylpyridinium acetate, 2,6-diacetyl-1-methylpyridinium-p-toluenesulfonate, 2,6-diacetyl-1-methylpyridinium benzenesulfonate, 2,6-diacetyl-1-methylpyridinium bromide, 2,6-diacetyl-1-methylpyridinium chloride, 2,6-diacetyl-1-methylpyridinium hydrogen sulfate or 2,6-diacetyl-1-methylpyridinium acetate.

5. Agent according to claim 1, wherein the 2-acylpyridinium derivatives of formula (I) are present in an amount of from 0.01 to 25 wt. %, based on total weight of the agent.

6. Agent according to claim 1, wherein the alkyl ether sulfate is a compound according to the formula R''—(OCH$_2$CH$_2$)$_n$—OSO$_3$M, wherein R'' is an optionally branched $C_8$-$C_{22}$ alkyl group and n is a number from 16 to 50.

7. Agent according to claim 1, wherein the alkyl ether sulfate is a compound according to the formula R''—(OCH$_2$CH$_2$)$_n$—OSO$_3$M, wherein R'' is a $C_{10}$-$C_{18}$ alkyl group and n is a number from 25 to 35.

8. Agent according to claim 1 further comprising at least one aromatic, organic solvent.

9. Agent according to claim 1 further comprising benzyl alcohol.

10. Agent according to claim 1 further comprising glycine and/or its physiologically acceptable salt.

11. Agent according to claim 1, wherein the agent has a pH of 7 to 11.

12. Agent according to claim 1 further comprising at least one inorganic persulfate or peroxodisulfate salt.

13. Agent according to claim 12, wherein the at least one inorganic persulfate or peroxodisulfate salt is chosen from ammonium peroxodisulfate, potassium peroxodisulfate and/or sodium peroxodisulfate.

14. Method for lightening keratin fibers comprising applying an agent according to claim 1 to keratin-containing fibers, leaving the agent on the fibers for 5 to 60 minutes, and rinsing out the agent or washing out the agent with a shampoo.

15. Kit of parts for lightening keratin fibers comprising, in separate containers:
   at least one oxidizing agent preparation (B) comprising hydrogen peroxide or a solid addition compound of hydrogen peroxide with inorganic or organic compounds, and
   at least one preparation (A) comprising, in a cosmetic carrier, at least one 2-acylpyridinium derivative of general formula (I) according to claim 1 and at least one alkyl ether sulfate.

* * * * *